United States Patent [19]

Manning et al.

[11] Patent Number: 4,465,078
[45] Date of Patent: Aug. 14, 1984

[54] METHOD FOR CELL SAMPLING IN A BODY CAVITY

[75] Inventors: Patrick R. Manning, Oakbrook; Donald W. West, Lake Forest, both of Ill.

[73] Assignee: Medtest Corporation, Lake Forest, Ill.

[21] Appl. No.: 429,689

[22] Filed: Sep. 30, 1982

[51] Int. Cl.³ .............................................. A61B 10/00
[52] U.S. Cl. ........................................ 128/759; 604/3
[58] Field of Search .......................... 128/754–759, 128/749, 750; 604/2, 3, 285, 286, 306, 904

[56] References Cited

U.S. PATENT DOCUMENTS

| | | | |
|---|---|---|---|
| Re. 29,061 | 12/1976 | Bucalo | 604/904 |
| 3,388,043 | 6/1968 | Ingvorsen | 195/139 |
| 3,450,129 | 6/1969 | Avery et al. | 128/2 |
| 3,792,699 | 2/1974 | Tobin | 604/2 |
| 3,796,211 | 3/1974 | Kohl | 128/2 B |
| 3,842,166 | 10/1974 | Bucalo | 424/9 |
| 3,918,435 | 11/1975 | Beall | 604/2 |
| 3,932,223 | 1/1976 | Bucalo | 195/139 |
| 3,979,263 | 9/1976 | Bucalo | 195/103.5 R |
| 4,223,093 | 9/1980 | Newman et al. | 435/295 |
| 4,252,904 | 2/1981 | Nelson et al. | 435/294 |
| 4,286,596 | 9/1981 | Rubinstein | 604/286 |

*Primary Examiner*—Kyle L. Howell
*Assistant Examiner*—Deidre A. Foley
*Attorney, Agent, or Firm*—Kirkland & Ellis

[57] ABSTRACT

A simple, inexpensive, accurate and potentially self-administered method for collecting human cells from a body cavity for cytodiagnosis.

8 Claims, 1 Drawing Figure

METHOD FOR CELL SAMPLING IN A BODY CAVITY

BACKGROUND OF THE INVENTION

1. Field of the Invention

This invention relates to a method for collecting human cells from a body cavity for subsequent testing and more particularly to a method for collecting such cells which may be self-administered.

2. Description of Prior Art

Since conception by Papanicolaou many years ago, the acceptance and utilization of cytodiagnosis has continued to expand. Today, a number of techniques involving multiple organ systems are available, all derived from the basic concept that comprehensive pathophysiologic changes may be recognized and evaluated a expressed at the cellular level.

Exfoliative cytology ("Pap test") has long been established as a highly accurate diagnostic tool allowing identification of a number of inflammatory, premalignant and malignant states or conditions. It has proven to be a critical technique in the early detection and treatment of lesions of the cervix and vaginal vault.

The simplicity of the procedure and its accuracy have resulted in its routine use by health care personnel and its wide acceptance by the patient population. Currently, the cell sampling is performed by a physician, nurse, or cytotechnologist using an applicator to obtain the appropriate cell sample. Smears are made immediately on slides which are then fixed to insure cell preservation and to eliminate artefactual changes which could result in misdiagnosis. There are several significant drawbacks with this technique:

1. It requires a trained health professional to take the smear. The time and cost involved thus deprive a significant portion of the population the opportunity of being tested for various pathophysiologic changes and conditions, including cancer.

2. The ability to make a satisfactory slide smear from the sample varies widely as does the expertise of those performing the test.

3. The inclusion of a pelvic examination in a physical examination is becoming less universal as medicine continues in its pattern of specialization. There is a definite trend, particularly in the United States, toward sending patients to a gynecologist for a pelvic exam and eliminating such an exam from the routine office physical.

It would be advantageous, therefore, if a modified cell sampling technique were available which would allow self administration, i.e., self sampling, combined with technical uniformity. The time and cost limitations in the use of the Pap test would thus be eliminated.

Accordingly, it is the principal object of the present invention to provide a simple, inexpensive and accurate method for self-administered cell sampling in a body cavity.

It is a further object of the present invention to provide a method for a self-administed cell sampling in a body cavity requiring minimal patient instruction.

SUMMARY OF THE INVENTION

In accordance with the subject invention, the foregoing objects have been achieved with an improved method for cell sampling in a body cavity comprising insertion into the body cavity of an absorbent carrier which contains an internal, rupturable fluid sac. In conjunction with insertion, the fluid sac is ruptured and the carrier moved or rotated in the body cavity such that a sample of human cells is collected from the walls of the body cavity and absorbed by the carrier. The carrier is then removed and the cell sample is transferred from the carrier to a medium for subsequent testing and analysis of the collected cells.

DETAILED DESCRIPTION OF THE PREFERRED EMBODIMENTS

Figure 1:
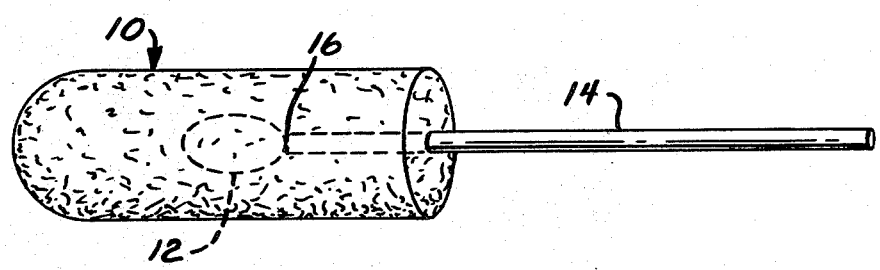
FIG. 1 is an schematic diagram of the device employed in accordance with the method of this invention.

Broadly described, this invention utilizes an absorbent carrier 10, preferably in a size and configuration enabling the device to be comfortably and conveniently introduced into a body cavity to remain temporarily therein and most preferably in the form and size of a conventional absorbent tampon, which has imbedded therein a rupturable sac containing sterile fluid 12, preferably sterile saline solution. The fluid is provided in an amount sufficient to maintain moistness at the surface of the carrier, preferably in an amount ranging from about 0.25 ml to about 3.0 ml and most preferably about 1.0 ml based on use in a conventional tampon-sized carrier. An excessive amount of fluid will result in sloughing off of the cell sample at the surface of the carrier. Insufficient fluid will cause the cell sample to dry out prematurely thereby destroying the cell morphology and rendering the sample unuseable for subsequent testing and analysis.

The absorbent carrier 10 is inserted into the body cavity, preferably the cervix and vaginal vault of the human female, by any of the variety of methods or devices conventionally used for insertion of a tampon 14. Immediately before, upon or after insertion, the rupturable sac 12 is ruptured, preferably by applying pressure to the rupturable sac or by insertion into the carrier 10 of an external object or by the force of resistance of the body against insertion of the absorbent carrier 10 operating against the end of the insertion device 16. The fluid is absorbed outward from the sac 16 to the surface of the absorbent carrier 10.

Upon reaching the region of the body cavity from which the cell sample is sought, the absorbent carrier 10 is moved with respect to the body cavity, preferably rotated about an axis through the center of the cavity and in the direction of the cavity, thereby collecting cells from the walls of the cavity. This movement may be accomplished by a variety of methods but preferably by translational or rotational movement of the insertion device 14. The cells adhere to the exterior surface of the absorbent carrier 10 where they are moistened and maintained at a moist level by the fluid from the rupturable sac 12, thereby preserving the sell morphology.

The absorbent carrier 10 is then removed from the body cavity by any of a variety of methods well-known in the art. The cell sample may be converted directly from the absorbent carrier 10 to a slide preparation by trained individuals according to any of a variety of methods well known in the prior art. Alternatively, the absorbent carrier 10 may be placed in an airtight container, which assures cell survival, for storage or for transport to trained individuals for conversion to a slide preparation. The slide preparation may then be used for cytodiagnosis.

We claim:

1. A method for collecting cells from a body cavity for cytodiagnosis, which comprises the steps of:
   (a) inserting into the body cavity an absorbent carrier having a rupturable sac of sterile fluid contained therein;
   (b) puncturing the rupturable sac of sterile fluid after insertion;
   (c) translating or rotating the absorbent carrier with respect to the body cavity thereby depositing on the absorbent carrier cells from the body cavity thereby forming a cell-laden carrier;
   (d) removing the cell-laden carrier from the body cavity; and
   (e) transferring the cells from the cell-laden carrier to a medium for cytodiagnosis.

2. The method of claim 1 wherein the body cavity is the human female cervix and vaginal vault.

3. The method of claim 1 wherein the absorbent carrier is an absorbent tampon having a rupturable sac of sterile fluid contained therein.

4. The method of claim 1 or claim 3 wherein the sterile fluid is sterile saline.

5. The method of claim 1 wherein the sterile fluid is provided in an amount ranging from about 0.25 ml to about 3.0 ml.

6. The method of claim 1 wherein the cell-laden carrier is placed in a substantially airtight container until said cells are transferred to the medium for cytodiagnosis.

7. The method of claim 1 wherein the cytodiagnosis comprises a test for pathophysiologic conditions.

8. The method of claim 1 wherein the cytodiagnosis comprises a test for carcinomia.

* * * * *